(12) United States Patent
Monte

(10) Patent No.: US 7,101,565 B2
(45) Date of Patent: Sep. 5, 2006

(54) PROBIOTIC/PREBIOTIC COMPOSITION AND DELIVERY METHOD

(75) Inventor: Woodrow C. Monte, Riverton (NZ)

(73) Assignee: Corpak MedSystems, Inc., Wheeling, IL (US)

( * ) Notice: Subject to any disclaimer, the term of this patent is extended or adjusted under 35 U.S.C. 154(b) by 411 days.

(21) Appl. No.: 10/068,750

(22) Filed: Feb. 5, 2002

(65) Prior Publication Data

US 2004/0086491 A2 May 6, 2004

(51) Int. Cl.
- A61K 2/02 (2006.01)
- A61K 9/48 (2006.01)
- A61K 9/20 (2006.01)
- A61F 13/02 (2006.01)

(52) U.S. Cl. .................. 424/423; 424/433; 424/451; 424/464

(58) Field of Classification Search .............. 424/423, 424/433, 451, 464
See application file for complete search history.

(56) References Cited

U.S. PATENT DOCUMENTS

| | | | |
|---|---|---|---|
| 3,884,827 A | 5/1975 | Asai | |
| 4,158,427 A | 6/1979 | Hegge | |
| 4,322,542 A | 3/1982 | Abbott | |
| 4,430,496 A | 2/1984 | Abbot | |
| 4,515,736 A | 5/1985 | Deamer | |
| 4,594,074 A | 6/1986 | Andersen et al. | |
| 4,772,471 A | 9/1988 | Vanlerberghe et al. | |
| 4,869,907 A | 9/1989 | Sasagawa | |
| 4,897,308 A | 1/1990 | Vanlerberghe et al. | |
| 4,960,589 A | 10/1990 | Sasagawa | |
| 5,049,489 A | 9/1991 | Aldrich et al. | |
| 5,319,116 A | 6/1994 | Viole et al. | |
| 5,329,020 A | 7/1994 | Kalota et al. | |
| 5,340,577 A | 8/1994 | Nisbet et al. | |
| 5,350,516 A | 9/1994 | Bhadra | |
| 5,373,085 A | 12/1994 | Fox et al. | |
| 5,374,425 A | 12/1994 | Porter | |

(Continued)

FOREIGN PATENT DOCUMENTS

| | | |
|---|---|---|
| WO | WO 01/01711 | 1/2001 |
| WO | WO/ 01/14322 | 3/2001 |
| WO | WO/ 01/14360 | 3/2001 |
| WO | WO/ 01/18048 | 3/2001 |
| WO | WO/ 01/21393 | 3/2001 |
| WO | WO/ 01/24675 | 4/2001 |

OTHER PUBLICATIONS

Madley, R. H., Associate Editor, Nutraceuticals World, "Probiotics, Prebiotics & Synbiotics: Harnessing Enormous Potential"; Sep. 2001 p. 50–76.

Mason, P., PhD, MRPharmS, "Probiotics and Prebiotics", The Pharmaceutical Journal vol. 266 No 7132 p. 118–121 Jan 27, 2001 [online] [retrieved Feb. 2, 2002] Retrieved from the Internet: <URL:http://www.pharmj.com/Editorial/20010127/education/education.html>.

(Continued)

Primary Examiner—Carlos A. Azpuru
(74) Attorney, Agent, or Firm—David E. Rogers; Allen J. Moss; Squire, Sanders & Dempsey L.L.P.

(57) ABSTRACT

A prebiotic, composition comprising a probiotic and prebiotic, and method of delivering a probiotic, prebiotic or composition directly into the intestinal tract of a mammal are disclosed. The probiotic is any beneficial bacteria and the prebiotic is a substance beneficial to a probiotic. Most preferably, the prebiotic includes a mucopolysaccharide. The method preferably involves delivering the prebiotic, probiotic or composition via a delivery tube, such as an enteral feeding tube, directly to a position downstream of the stomach, most preferably to the jejunum.

59 Claims, 1 Drawing Sheet

U.S. PATENT DOCUMENTS

| | | | |
|---|---|---|---|
| 5,424,299 | A | 6/1995 | Monte |
| 5,443,651 | A | 8/1995 | Kalota et al. |
| 5,449,748 | A | 9/1995 | Ramsey |
| 5,470,942 | A | 11/1995 | Alexander et al. |
| 5,478,557 | A | 12/1995 | Nisbet et al. |
| 5,501,857 | A | 3/1996 | Zimmer |
| 5,531,988 | A | 7/1996 | Paul |
| 5,533,540 | A | 7/1996 | Stanasolovich et al. |
| 5,552,517 | A | 9/1996 | Martin |
| 5,604,127 | A | 2/1997 | Nisbet et al. |
| 5,670,483 | A | 9/1997 | Zhang et al. |
| 5,691,185 | A | 11/1997 | Dickely et al. |
| 5,721,345 | A | 2/1998 | Roberfroid et al. |
| 5,733,540 | A | 3/1998 | Lee |
| 5,744,134 | A | 4/1998 | Paul |
| 5,824,469 | A | 10/1998 | Horwitz et al. |
| 5,840,361 | A | 11/1998 | Theuer et al. |
| 5,856,427 | A | 1/1999 | Chou |
| 5,865,427 | A | 2/1999 | Cowan |
| 5,866,385 | A | 2/1999 | Dickely et al. |
| 5,876,990 | A | 3/1999 | Reddy et al. |
| 5,879,719 | A | 3/1999 | Valentine |
| 5,886,165 | A | 3/1999 | Kandimalla et al. |
| 5,895,648 | A | 4/1999 | Cavaliere Vesely et al. |
| 5,902,578 | A | 5/1999 | Halpin-Dohnalek et al. |
| 5,902,743 | A | 5/1999 | Luchansky et al. |
| 5,906,996 | A | 5/1999 | Murphy |
| 5,908,783 | A | 6/1999 | Brewer |
| 5,922,345 | A | 7/1999 | Horrobin et al. |
| 5,922,375 | A | 7/1999 | Luchansky et al. |
| 5,955,343 | A | 9/1999 | Holmes et al. |
| 5,962,046 | A | 10/1999 | Eyer et al. |
| 5,968,569 | A | 10/1999 | Cavadini et al. |
| 6,010,695 | A | 1/2000 | Line et al. |
| 6,010,725 | A | 1/2000 | Meister et al. |
| 6,017,525 | A | 1/2000 | Logan et al. |
| 6,020,139 | A | 2/2000 | Schwartz et al. |
| 6,022,568 | A | 2/2000 | Lesens et al. |
| 6,030,650 | A | 2/2000 | Kamarci |
| 6,054,148 | A | 4/2000 | Rust et al. |
| 6,056,979 | A | 5/2000 | Benbadis et al. |
| 6,057,424 | A | 5/2000 | Vail, III |
| 6,060,050 | A | 5/2000 | Brown et al. |
| 6,068,862 | A | 5/2000 | Ishihara et al. |
| 6,077,504 | A | 6/2000 | Vesley et al. |
| 6,080,401 | A | 6/2000 | Reddy et al. |
| 6,090,417 | A | 7/2000 | Mehnert et al. |
| 6,093,425 | A | 7/2000 | Kamarei |
| 6,100,388 | A | 8/2000 | Casas et al. |
| 6,107,033 | A | 8/2000 | Welling et al. |
| 6,110,676 | A | 8/2000 | Coull et al. |
| 6,117,477 | A | 9/2000 | Paluch |
| 6,132,710 | A | 10/2000 | Panigrahi et al. |
| 6,149,965 | A | 11/2000 | van Lengerich et al. |
| 6,159,710 | A | 12/2000 | Fraser et al. |
| 6,180,099 | B1 | 1/2001 | Paul |
| 6,200,605 | B1 | 3/2001 | Day |
| 6,200,609 | B1 | 3/2001 | Meister et al. |
| 6,203,797 | B1 | 3/2001 | Perry |
| 6,217,915 | B1 | 4/2001 | Luchansky et al. |
| 6,221,350 | B1 | 4/2001 | Brown et al. |
| 6,225,063 | B1 | 5/2001 | Khvorova et al. |
| 6,231,863 | B1 | 5/2001 | Colau et al. |
| 6,241,983 | B1 | 6/2001 | Paul et al. |
| 6,242,194 | B1 | 6/2001 | Kullen et al. |
| 6,254,886 | B1 | 7/2001 | Fusca et al. |
| 6,254,910 | B1 | 7/2001 | Paluch |
| 6,255,080 | B1 | 7/2001 | Teather et al. |
| 6,258,847 | B1 | 7/2001 | Chachoua |
| 6,262,019 | B1 | 7/2001 | Keller et al. |
| 6,274,564 | B1 | 8/2001 | Sarill et al. |
| 6,274,567 | B1 | 8/2001 | Brown et al. |
| 6,309,666 | B1 | 10/2001 | Hatano et al. |
| 2003/0118571 | A1 * | 6/2003 | Reid et al. ............... 424/93.45 |

OTHER PUBLICATIONS

Michetti, P., MD, "Lactobacilli for the Management of Helicobacter pylori", Natren [online] [retrieved Feb. 1, 2002] Retrieved from the Internet: <URL:http://www.natren.com/pages/natashart7.html>.

Trenev, N., "Probiotics: The Foundation of Your Health, Now and Forever", Natren [online] [retrieved Feb. 1, 2002] Retrieved from the Internet: <URL:http://www.natren.com/pages/natashart4.html>.

VTT Biotechnology, Anaerobic Microbiology, [online] [retrieved Feb. 1, 2002] Retrieved from the Internet: <URL:http://www.vtt.fi/bel/2000microbiology/anaerobic_microbiology/>.

Goodman, S., Ph.D., "The Evidence for Probiotics", Positive Health [online] [retrieved Feb. 1, 2002] Retrieved from the internet: <URL:http://www.positivehealth.com/permit/Articles/Colon%20Health/evidence.html>.

Potera, C., "Probiotics Gaining Recognition", ASM News (American Society for Microbiology) vol 65, Num 11, Nov. 1999, [online] [retrieved online Feb. 1, 2002] Retrieved from the Internet: <URL:http://www.asmusa.org/memonly/asmnews/nov99/topic5.html>.

Department of Cariology, Faculty of Odontology, Malmo University Sweden, "Lactobacilli—Oral Health", [online] [retrieved online Feb. 1, 2002]Retrieved from the Internet: <URL:http://www.db.odont.lu.se/lbcgen.html>.

Flora Source, "The Health Revolution", [online] [retrieved online Feb. 1, 2002] Retrieved from the Internet: <URL:http://santee.tripod.com/FLORA–SOURCE–2.html>.

Imperial Sensus, "What Does Frutafit–Inulin Do?" [online] [retrieved online Dec. 9, 2001] Retrieved from the Internet: <URL:http://www.imperialsensus.com/whatis.html>.

OraftI, The Raftilose Family, [online] [retrieved online Apr. 12, 2002] Retrieved from the Internet:<URL: http://www.orafti–us.com/raftilose.html>.

Matsutani Chemical Industry Co., Fibersol 2, [online] [retrieved online Dec. 9, 2001] Retrieved from the Internet: <URL:http://www.matsutani.com/fibersol2main.html>.

PURAC, Product Line [online] [retrieved online Dec. 9, 2002] Retrieved from the Internet: <URL:http://www.purac.com/products.html>.

Stonyfield Farm, Oh joy, it's Soy! Healthy Food, [online] [retrieved online Dec. 9, 2002] Retrieved from the Internet: <URL:http://www.stonyfield.com/HealthyFood/Organic-CulturedSoy.shtml>.

Elixa, Friendly Colonizer Probiotic Formula with SBOs, [online] [retrieved online Feb. 1, 2002] Retrieved from the Internet:<URL:http://www.elixa.com/nutrient/colonizer.htm.

MBA Company, GastroIntestinal Health, [online] [retrieved Dec. 9, 2000] Retrieved from the Internet: <URL:http://www.merc–buyers.com/numero–99.htm>.

NPI International Corp., Company Profiles, [online] [retrieved Dec. 9, 2001] Retrieved from the Internat: <URL:http:// . . . /company.asp?ProductId=4253&id=12926&content=viewproducts&action=compa.

Nebraska Cultures, Products, [online] [retrieved online Apr. 12, 2002] Retrieved from the Internet: <URL:http://nebraskacultures.com/lacto.html>.

VALIO, Your Guide to Lactobacillus GG, [online] [retrieved online Apr. 12, 2002] Retrieved from the Internet: <URL:http://www.valio.fi/lgg/>.

Imperial–sensus, What is Frutafit–inulin? [online] [retrieved online Dec. 9, 2001] Retrieved from the Internet: <URL:http://www.imperialsensus.com/whatis.html>.

GTC Nutrition Company, NutraFlora, [online] [retrieved online Dec. 9, 2001] Retrieved from the Internet: <URL:http://www.gtcnutrition.com/chpnffaqs.html>.

ORAFTI, The Raftiline Family, [online] [retrieved online Dec. 9, 2001] Retrieved from the Internet: <URL:http://www.orafti–us.com/raftiline.com.

Probiohealth, About Probiotics, [online] [retrieved online Feb. 1, 2002] Retrieved from the Internet: <URL:http://www.probiohealth.com/ph–probiotics.html>.

Cascade Fresh, The Eight Active Cultures in Cascade Fresh, [online] [retrieved online Feb. 1, 2002] Retrieved from the Internet: <URL:http://www.cascadefresh.com/cultures.html>.

Family Health News, "Finding Bacteria Friendly", [online] [retrieved online Apr. 12, 2002] Retrieved from the Internet: <URL:http://www.familyhealthnews.com/art_probiotic_bacteria.htm>.

Imperial–Sensus, History of Inulin Consumption, [online] [retrieved online Apr. 12, 2002] Retrieved from the Internet: <URL:http://www.imperialsensus.com/history.html>.

* cited by examiner

PROBIOTIC/PREBIOTIC COMPOSITION AND DELIVERY METHOD

FIELD OF INVENTION

The present invention relates to a prebiotic, a composition comprising a prebiotic and a probiotic, and a method of administering either a prebiotic, a composition or a probiotic directly into the intestinal tract of a mammal.

BACKGROUND OF THE INVENTION

For the purpose of this application, the following terms have the following meanings: "Probiotic" means live bacteria (also called microflora or microorganisms) that confer a beneficial effect when an effective amount is introduced into the intestinal tract of a mammal. "Prebiotic" means any substance that can be consumed by a relevant probiotic, or that otherwise assists in keeping the relevant probiotic alive or stimulates its growth, and includes mucopolysaccharides, oligosaccharides, polysaccharides, amino acids, vitamins, nutrient precursors and proteins. "Compliment" or "complimentary" with respect to a prebiotic means that the prebiotic is consumed by, or otherwise assists in keeping alive or stimulates the growth of, a relevant probiotic. "Beneficial substance" means a prebiotic, probiotic or composition comprising probiotic and prebiotic. "Effective amount" means any non-zero amount of a beneficial substance that is introduced into the intestinal tract of a subject, wherein the beneficial substance is not inherently present in food stuffs being introduced into the subject's gastrointestinal tract. "Intestinal tract" or "gastrointestinal tract" means the tract from the mouth to the anus and includes the stomach and intestines (including the ileum, duodenum, jejunum, caecum, crasum (large intestine), rectum, and tenue (small intestine, which includes the tenue mesenteriale). "Delivery tube" means any passageway or conduit inserted into or otherwise placed in the body for introducing a beneficial substance directly into a part of the intestinal tract, and includes enteral feeding tubes. "Downstream" or "beneath" means any part of the intestinal tract downstream of the organ referenced. "Upstream" means any part of the body upstream of the organ referenced. "Subject" means a mammal to which a beneficial substance is administered.

Certain bacteria (included in the foregoing definition of probiotic) have been shown to be beneficial to human gastrointestinal health. The human gastrointestinal tract contains an estimated $100 \times 10^9$ viable bacteria, representing as many as 100 or more different species. About Probiotics, www.probiohealth.com. While few microorganisms are found in the stomach because of its high acidity, their numbers increase downstream of the stomach. Natasha Trener, Probiotics: The Foundation of Your Health, Now and Forever (Excerpts), www.natren.com. The greatest numbers and variety are found in the large intestine. Id.

Probiotics assist in keeping harmful pathogenic species in check. At least some probiotics attach to the intestinal wall and produce a mildly acidic environment (in part due to the excretion lactic acid) that curbs the growth of certain harmful, disease-causing bacterial species. About Probiotics, supra. Probiotics are also believed to assist in important nutrient assimilation, producing many important enzymes and potentially increasing the bioavailability of, and synthesizing, some vitamins (particularly the Bs and K), fatty acids, lactase, and calcium. Why You Need to Take The Friendly Probiotic Bacteria in Friendly Colonizer, www.elexacom.

Among other benefits conferred by probiotics are believed to be: strengthening of the immune system, neutralization of toxins, normalization of bowel movements, control of cholesterol, countering of allergies and skin problems, and the prevention of yeast and fungal infections. About Probiotics, supra; Probiotics: The Foundation of Your Health, Now and Forever, supra; Why You Need to Take the Friendly Probiotic Bacteria for Friendly Colonizer, supra.

The major bacteria in the intestines can be roughly divided into three groups: (a) lactic acid bacteria, including Lactobacilli, Bifidobacteria, and streptococci; (b) anaerobic bacteria; and (c) aerobic bacteria. At least Lactobacilli, Streptococci, and Bifidobacteria confer beneficial effects to mammals, particularly humans, and are included in the definition of probiotic herein.

Lactobacilli (i.e., bacteria of the genus *Lactobacillus*, abbreviated as "L.") have been used for several hundred years as food presentations and for promoting human health. About Probiotics. supra Lactobacilli found in the human intestinal tract include *L. acidophilus, L. casei, L. fermentum, L. saliva roes, L. brevis, L. leichmannii, L. plantarum,* and *L. cellobiosus.*

*L. acidophilus* has been shown to be useful in treating conditions such as antibiotic-induced imbalances in the gastrointestinal microflora, hypercholesterolemia, vaginal infections, *E. coli* infection, depressed immunity, cancerous tumors, chronic granulomatous disease, and lactose indigestion. A. G. Shauss, Method of Action, Clinical Application, and Toxicity Data, 3 *J. Advancement Med.* 163 (1990). It has also been shown that the activities of fecal bacterial enzymes thought to play a role in conversion of procarcinogens to carcinogens, such as betaglucuronidase, glucuronidase, nitroreductase, and azoreductase, were reduced 2- to 4-fold in persons taking *L. acidophilus* supplements. B. R. Goldin & L. S. Gorbach, "The Effect of Milk and *Lactobacillus* Feeding on Human Intestinal Bacterial Enzyme Activity," 39 *Amer. J. Chin. Nutr.* 756 (1984). These results suggest that dietary supplementation with *L. acidophilus* may reduce the risk of developing colon cancer.

Lactobacilli also produce organic acids that reduce intestinal pH thereby inhibiting the growth of acid-sensitive undesirable bacteria. *Why You Need to Take the Friendly Probiotic Bacteria for Friendly Colonizer,* supra. Lactobacilli produce lactic acid, hydrogen peroxide, and possibly acetic and benzoic acids. In vitro studies have shown *L. acidophilus* to inhibit the growth of pathogenic bacteria such as *Campylobacter pylori, Staphylococcus aureus, Pseudomonas aeruginosa,* and *Sarcina lutea.* K. M. Shahani et al., "Natural Antibiotic Activity of *Lactobacillus Acidophilus* and *Bulgaricus*," 11*Cultured Dairy Products J.* 14(1976).

Bifidobacteria are also known to exert a beneficial influence on human health. These bacteria exert antimicrobial activity in the human intestine by producing short chain fatty acids (SCFAs) such as acetic, propionic, and butyric acids, as well as lactic and formic acids, as a result of carbohydrate metabolism. The most plentiful SCFA produced by Bifidobacteria is acetic acid, which is an antimicrobial to gastrointestinal pathogens such as yeasts, molds, and certain other bacteria. Further, both Lactobacilli and Bifidobacteria may produce other antimicrobial substances, such as bacteriocins, that also inhibit the growth and proliferation of certain harmful bacteria.

Additionally, SCFAs are believed to support normal gastrointestinal function by increasing colonic blood flow, stimulating pancreatic enzyme secretion, promoting sodium and water absorption and intestinal mucosal growth. Bifidobacteria are also believed to deconjugate bile salts to free bile acids, which are more inhibitory to susceptible bacteria than are the conjugated forms.

Therapeutic applications of Bifidobacteria are used to treat diarrhea, constipation, and hepatic encephalopathy with hyperammonemia. Additional benefits are believed to include the production of B vitamins and breakdown of carcinogenic N-nitrosamines.

Bifidobacteria constitute the predominant microorganisms in the fecal microflora of week-old breast-fed infants, making up 85–99% of the bacterial population. Upon weaning or upon an event such as an infection, vaccination, or a sudden change in diet, the balance of microorganisms in the gastrointestinal tract of these babies can be upset. The Bifidobacterial population in adults is generally stable. However, changes in diet, administration of antibiotics, exposure to gamma radiation or X-rays, disease, pollutants, stress, or other disturbances can result in an overgrowth of potentially pathogenic bacteria and/or a decrease in beneficial bacteria (e.p., Lactobacilli and/or Bifidobacteria). *About Probiotics*, supra. Bifidobacteria numbers can be significantly reduced in elderly people for other reasons, for example, due to a reduction of secreted gastric juices.

Without sufficient numbers of probiotics, intestinal ecology may be thrown off balance, which can potentially result in health problems. Probiotic supplements may be used to increase the number of probiotics in the intestinal tract. *About Probiotics*, supra. As mentioned in "Probiotics, Prebiotics & Synbiotics: Harnessing Enormous Potential," *Nutraceuticals World* (September 2001), a trend regarding probiotics is finding novel delivery systems, particularly because acidity in the stomach is detrimental to many probiotics and may destroy as much as 90–95% of such probiotics during their passage through the stomach. To date, improving the protection of probiotics from stomach acid has included using enteric coated capsules and microencapsulation. Such types of microencapsulation include technology known as Probiocap™ by Institut Rosell.

Known prebiotics include dietary fibers, such as polysaccharides and oligosaccharides, that have the ability to increase the number of probiotic, which leads to the benefit(s) conferred by the probiotic. For example, an increase of beneficial Bifidobacteria is likely to change the intestinal pH to support an increase of Bifidobacteria, and which decreases pathogenic organisms. A prebiotic may also provide one or more of the following benefits: (1) indirectly produce short chain fatty acids (SCFAs) that in turn have a trophic (nourishing) effect on the intestinal epithelium, supporting its integrity as a defense barrier against invading organisms; (2) indirectly produce immune stimulants, by the promotion of Bifidobacteria that excrete an end product inhibitory to pathogenic bacteria; (3) promote a host-mediated attack against tumor sites and promote certain strains of Lactobacilli that have immune-modulating activity, enhancing phagocyte activity in the blood; and (4) indirectly provide any of the benefits of an increased number of probiotic whose number increased due at least in part to the presence of the prebiotic. A prebiotic may also affect the production of certain bacteria enzymes, such as decreasing glucosidase that is associated with the absorption of intestinal cholesterol, associated with the formation of secondary bile acid that is considered a co-carcinogen.

However, while known prebiotics break down to provide carbohydrates for probiotics, some probiotics also require amino acids for nourishment.

It would therefore be desirable to have a prebiotic that was resistant to stomach acids and that provided carbohydrates and amino acids to support probiotic growth. It would also be desirable to introduce a probiotic into the intestinal tract in a manner that alleviates the destruction caused by stomach acid and enables the probiotic to quickly enter the intestines, where it can be of most benefit.

SUMMARY OF THE INVENTION

One aspect of the invention is a novel prebiotic comprising a mucopolysaccharide. Preferred mucopolysaccharides are chitin, agar and carraganan. Mucopolysaccharides are resistant to stomach acids; much of a mucopolysaccharide passes through the stomach to the intestines where it is digested by one or more probiotics. Mucopolysaccharides decompose into carbohydrates and amino acids, thus providing high-quality nourishment for certain probiotics. The most preferred prebiotic according to the invention comprises a mucopolysaccharide and an oligopolysaccharide.

Another aspect of the invention is a composition comprising a probiotic and prebiotic, wherein the prebiotic is selected to compliment a relevant probiotic and preferably includes a mucopolysaccharide. Mucopolysaccharides tend to agglomerate when wet, forming a globule having a mucous-like or gelatinous coating and a relatively dry interior. Probiotics in the interior of such a globule are at least partially protected from stomach acids and, if the composition passes through the stomach, a greater number of probiotic survives and enters the intestines alive.

The invention also includes a novel method for delivering a beneficial substance directly into the intestinal tract, preferably downstream of the stomach, and most preferably into the jejunum. The method preferably utilizes a delivery tube, such as an enteral feeding tube, through which the beneficial substance is conveyed directly into the intestines. In that manner the beneficial substance is delivered directly to where it can provide beneficial results (ultimately, an increase in the number of probiotic) and avoid most of the stomach acids.

Any aspect of the present invention that requires the introduction of a beneficial substance into the gastrointestinal tract of a subject requires that an effective amount be introduced.

DETAILED DESCRIPTION OF A PREFERRED EMBODIMENT

Figure 1:
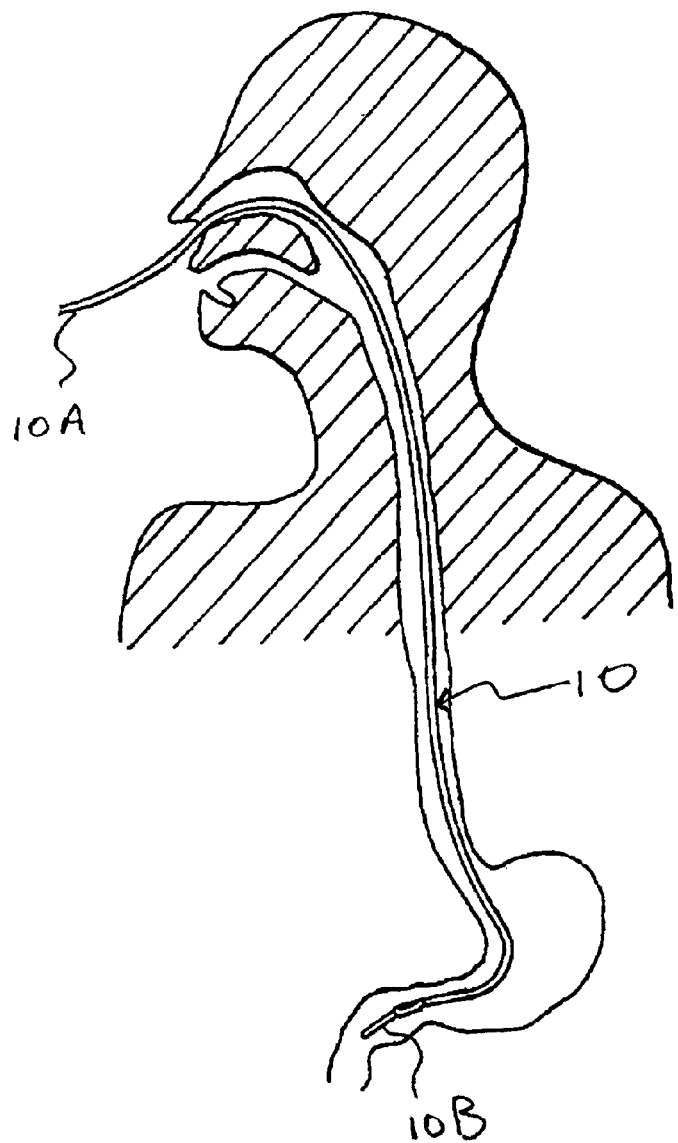
FIG. 1 shows a cross-sectional view of an abdomen including a delivery tube that may be used to practice the invention.

The invention comprises one or more of the following: (a) a novel prebiotic, namely a mucopolysaccharide, (b) a composition comprising a prebiotic (preferably including a mucopolysaccharide) and a probiotic, and/or (c) a method for delivering a beneficial substance directly into the intestinal tract downstream of the stomach, most preferably into the jejunum.

As used in this specification and the appended claims, the singular forms "a," "an," and "the" include both the singular and the plural unless the context clearly dictates otherwise. For example, a composition containing "a probiotic" includes a composition having one probiotic or two or more probiotics, and "a prebiotic" includes a prebiotic or two or more prebiotics. Each of the terms "includes," "include,"

"comprises" and "comprise" means "includes at least." For example, "a prebiotic comprising FOS" means the prebiotic includes at least FOS; it may also include other prebiotics and/or other substances.

Probiotics that may be used to practice the invention are bacteria that benefit mammalian (particularly human) health, particularly gastrointestinal health. Preferably, the probiotic includes one or more of a Lactobacilli and Bifidobacteria Specific probiotics that may be used include, but are not limited to, one or more of *L. acidophilus, L. reuteri, L. curvatus, L. bulgaricus, L. grasseri, L. casei, L. fermentum, L. caveasicus, L. helveticus, L. lactis, L. salivarius, L. rhamnosus, L. brevis, L. leichmanni, L. plantarum, L. cellobiosus, L. buchneri, Bifidobacterium* (abbreviated as "B,") *laterosporus, B. breve, B. subtilus, L. sporogenes* (also known as *Bacillus coagulans*), *pediococcus acidilactici, pediococcus pentosaceus, enterococcus faecium, B. adolescentis, B. infantis, B. longum, B. thermophilum, B. animalis*, and *B. bifidum. Steptococcus thermphilius* may also be used, which is believed to improve lactose digestion and make micronutrients more available to the host. *The Eight Active Cultures in Cascade Fresh*, www.cascadefresh.com. Other probiotics that may be used include *Lactococcus lactis cremoris, S. diacetylactis* and *S. intermedius*. Most preferably, the probiotic includes one or more of *L. acidophilus, B. adolescentis* and *B. bifidum*.

Commercially available strains of *L. acidophilus* include NCRM and *Lactobacillus acidophilus* DDS-1, manufactured by Nebraska Cultures, Inc. and *Lactobacillus rhamnosus* GG, manufactured by LGG—Research and Development, which is deposited in the American Type Culture Collection, coded ATCC 53103. Another commercially available strain of Lactobacilli is KE-99 LACTO by Probiohealth, Inc. of Los Angeles, Calif.

In addition to the benefits already described herein, a brief description of some benefits attributed to some of the preferred probiotics follows: *L. casei* is highly prolific and hardy. It produces lactic acid and digests a wide range of carbohydrates. Because of its ability to eliminate protein wastes from the intestine before they enter the bloodstream, it is believed to benefit the immune system. *L. plantarum* produces lactic acid and acts as a natural antibiotic (as acidophilin). *L. salivarius* is effective in eliminating bowel toxemia, and it produces B and K vitamins, enzymes, and lactic acid, and aids in the production of lactase. *L. bulgaricus* produces lactic acid and enhances the digestion of milk sugar. *Streptococcus thermophilus* produces lactic acid and lactase.

There is no published standard for the amount of bacteria that should be in a probiotic product or dosage, only estimated figures ranging from $10^6$ to $10^{10}$ bacteria per day, depending on the condition of the host. However, probiotics are generally safe and well tolerated by humans even at high dosages.

A prebiotic according to the invention is complimentary to at least one probiotic (a) present in a composition according to the invention, (b) administered separately to a subject to whom the prebiotic is administered, and/or (c) already present in the gastrointestinal tract of a subject to whom the prebiotic is administered. Determining whether a prebiotic is complimentary to a probiotic may be done in a number of ways known to those skilled in the art. For example, the effect could be gauged by a plate count of probiotic present in a subject's feces or the pH of a subject's chyme, a lowering of which would likely indicate an increased number of probiotic. Alternatively, a probiotic could be cultured in vitro with a selected prebiotic and without the probiotic. Tests could then be conducted to determine relative growth curves over time.

The prebiotic may comprise one or more of the following (a) an oligosaccharide, (b) a fructo-oligosaccharide ("FOS"), such as a soy fructo-oligosaccharide, inulin or banana fiber, (c) a pectin or pectic polysaccharide, (d) a mannan, such as guar gum, locust bean gum, konjac, or xanthan gum, (e) a pentosan, beta-glucan, arabinan and galactan, such as larch arabinogalactan, and (f) mixtures thereof.

FOS are long-chain polysaccharides comprised primarily of fructose monosaccharides bonded together by 1-β-D-fructofuranosyl linkages. Upon ingestion, fructo-oligosaccharides are only partially hydrolyzed as they pass through the mouth, stomach, and small intestine. In the large intestine, they became food for certain probiotics, such as *L. acidophilus* and *B. infantis* and are metabolized into SCFAS, mainly acetic, propionic, butyric, and lactic acids. As a consequence of this fermentation, a considerable amount of bacterial mass is produced. This results in increased numbers of probiotic, a lowered intestinal pH, and is believed to inhibit pathogens. A pH decrease will increase solubility of calcium and other minerals and may enhance the absorption of calcium and magnesium. Illustrative fructo-oligosaccharides include inulin, banana fiber, and soy fructo-oligosaccharides, and are found in honey, beer, onion, asparagus, Chinese chive, maple sugar, oats, and Jerusalem artichoke.

Inulin is produced naturally in an estimated 36,000 or more plants worldwide including onion, asparagus, artichoke, and many cereals. Chicory root and Jerusalem artichoke each contain a significant amount of inulin. In addition to encouraging the growth of probiotics, some animal studies and some human clinicals suggest that inulin oligosaccharides provide the benefit of enhancing calcium and magnesium absorption in the small intestine.

The pectins and pectic polysaccharides (high and low methoxyl pectins) may also be used as a prebiotic. Pectin is a highly water soluble, noncellulosic polysaccharide fiber that occurs naturally as a partial methyl ester of α-(1→4) linked D-polygalacturonate sequences interrupted with (1→2)-L-rhamnose residues. The term pectic polysaccharides refers to galacturonans or, more commonly, rhamnogalacturonans wherein (1–4)-α-D-galacturonan chains are interrupted at intervals by insertion of (1–2)-α-L-rhamnose residues. Other constituent sugars attached as side chains include D-galactose, L-arabinose, D-xylose, and, less frequently, L-frucose and D-glucuronic acid. Most of these sugars occur in short side chains, although D-galactose and L-arabinose are found in multiple units. Extremely complicated side chains containing neutral pectic polymers such as galactans and arabinans, xyloglucans, and galactomannans have been reported.

Pectin is usually extracted from the primary cell walls of certain plants. Rich sources of pectin include lemon and orange rinds, which contain about 30% by weight of pectin. Pectins are used as gelling and thickening agents in food technology and as an antidiarrheal in veterinary medicine.

Mannans (such as glucomannans and galactomannans), such as guar gum, locust bean gum, konjac, and xanthan gum, are present in some plant cell walls. The glucomannans are generally comprised of (1–4)-β-linked glucose and mannose units, while the galactomannans are generally comprised of a (1–4)-β-mannan backbone substituted with single units of (1–6)-α-galactose. Many endospermic legumes, such as guar and locust bean, contain galactomannans in the endosperm during seed development. Glucomannans have also been found as a minor component of cereal grains.

Guar gum is produced from the ground endosperms of *Cyamopsis tetragonolobus*, a legume cultivated in India as a livestock feed. The water soluble fraction, which typically comprises about 85% of guar gum is also known as guaran.

Arabingalactans ("AG") are non-starch polysaccharides used as a dietary fiber, and which exist in many edible sources including carrots, larch, radishes, black beans, pears, maize, wheat, red wine, tomatoes and coconuts. AG resists digestion by the enzymes in saliva and the small intestine and enters the large bowel where it is fermented by at least some of the resident probiotics. Studies have shown that the majority of probiotics that ferment AG are Bifidobacterium. Fermentation of AG by various species of these genera produce SCFAs that lower colon pH, favoring the growth of these probiotics and acting as a natural antimicrobial agent, as previously mentioned. This is believed to lead to a lowering of ammonia in the colon, which is a distinct benefit since excess ammonia is associated with an increase in carcinogenic activity.

The production of SCFAs from the AG fermentation leads to relatively high butyrate concentrations. In addition to butyrate's trophic effects on mucosa, it is believed to be beneficial to the colon epithelium. Further, a defect in butyrate metabolism has been identified in ulcerative colitis patients. At least one comparison of the fermentation of AG and other polysaccharides showed that AG produced significantly more butyrate than either pectin or xylan. Both animal and human studies have shown a reduction of pathogenic bacteria in the colon when AG is consumed, and an increase in *B. longum*.

Some specific commercial prebiotics that may be used to practice the invention include (1) FOS such as BeFlora™, manufactured by Triarco Industries, Wayne, N.J.; (2) short chain FOS, such as NutraFlora®, distributed by GTC Nutrition, Golden Colo.; (3) inulin, such as Raftiline® and Raftilose®, manufactured by Orafiti of Malvern, Pa., Frutafit® by Imperial Sensus of Sugarland, Tex., and Inuflora™, manufactured by Marlyn Neutraceuticals of Phoenix, Ariz.; (4) resistant starch, such as Hi-Maize™, manufactured by Imperial Sensus; (5) starches such as Fibersol-2™, manufactured by Matsutani America, Decatur, Ill., and which is derived from natural corn starch, (6) larch arabinogalactan AG derived from the Larch tree, and (7) Lacty® derived from lactitol, which is a hydrogenated lactose manufactured by Purac America, Lincolnshire, Ill., Polylactose could also be used, if available.

A preferred prebiotic is a mucopolysaccharide. As previously discussed, some benefits of mucopolysaccharides are:

(a) they are not readily digested by stomach acids;

(b) they tend to agglomerate when wet, forming globules with a gelatinous exterior and relatively dry interior; probiotics in the interior are at least partially protected from stomach acids; and (c) they decompose to provide both carbohydrates and amino acids to probiotics.

Mucopolysaccharides are a class of polysaccharide molecules, also known as glycosaminoglycans, composed of amino-sugars chemically linked into repeating units that give a linear unbranched polymeric compound. The amino-sugar constituents are typically ordinary monosaccharides that contain a nitrogen atom covalently bound to one of the ring carbons of the sugar portion. The nitrogen is, in turn, either bonded to two atoms of hydrogen (termed a primary amnino-group) or to another carbon atom (hence, a substituted amino-group). The mucopolysaccharides are similar structurally to animal and plant polysaccharides such as glycogen and starch. Chitin is a particularly plentiful mucopolysaccharide and is found in the shells of lobsters, crayfish, crabs, insects, and many other invertebrate organisms. The copepods, a group of microscopic marine organisms of the class Crustacea, alone are considered to synthesize about $10^9$ tons of chitin per year.

Heparin, an anticoagulant used widely in the treatment of blood clotting disorders, such as pulmonary embolus, is another mucopolysaccharide, although it is not preferred for practicing the invention. Another mucopolysaccharide is hyaluronic acid, a molecule found universally in the connective tissues of animals and in the fluids of their eyes and joints. Hyaluronic acid in association with protein has been isolated from various organisms. Some other mucopolysaccharides include agar, carraganan and other mucopolysaccharides extracted from seaweed, which are available through various companies such as FMC Marine Colloids.

A beneficial substance according to the invention may be provided and/or used in any manner or form; if a delivery method is specified, the beneficial substance is supplied in a form suitable to the delivery method. Most preferably the beneficial substance is first prepared as a dried and ground particulate, and then added to a liquid before administration to a subject. If the beneficial substance includes mucopolysaccharides or gums, it preferably agglomerates when the water is added.

A composition according to the invention includes a probiotic and a prebiotic. Preferably the prebiotic compliments the probiotic in the composition, but the prebiotic may compliment another probiotic, such as one present in the intestines but not in the composition. Most preferably, a prebiotic used in a composition includes a mucopolysaccharide. Any mucopolysaccharide, either plant (such as agar) or animal (such as chitin) may be used.

A beneficial substance is preferably provided freeze dried and ground into a fine powder. Probiotic may be provided already ground or may be ground using any suitable method or system, such as a hammer mill. Commercial sources for freeze-dried and/or ground probiotics are available and known to those knowledgeable in the art of probiotics. Prebiotic is preferably formed or ground into a fine dry powder (using any suitable method or system, such as a hammer mill) having a particle size equal to or less than 25 microns. The probiotic and prebiotic may be ground together into a composition, or the ground prebiotic and ground probiotic may be mixed using any suitable method or system, such as a ribbon blender. If ground with the prebiotic, the probiotic would have the same particle size as the prebiotic. If administered via a delivery tube, as discussed in more detail below, the particle size of the beneficial substance should be small enough to enable the beneficial substance to be suspended in a liquid and pass through the delivery tube.

In addition, a probiotic may be grown in any suitable prebiotic, including a mucopolysaccharide or prebiotic including a mucopolysaccharide. Such as a probiotic culture and prebiotic could then be freeze dried and ground together to form a composition.

The preferred composition would consist of up to 20% (0.1–99%) probiotic and up to 99.9% (1–99.9%) prebiotic. A composition may be delivered in combination with any other substance or compound, such as enteral food, as long as the other substance or compound does not destroy the ability of the beneficial substance to confer a beneficial effect. For example, the composition may comprise prebiotics other than those specifically described herein, such as bifidius factor (currently available only from human milk), minerals, vitamins, phytochemicals, enzymes, lactoperoxidase, thiocyanate salt, lactoferrin, gluconic acid, phytochemical, amino acids and/or other substances that may benefit the probiotic of choice or otherwise benefit the subject.

A beneficial substance including mucopolysaccharide may be ingested orally, either as a tablet, capsule or drink. Or, the beneficial substance including a mucopolysaccharide or gum may be placed in powder form into agglomerator where moisture is sprayed onto it to form globules having a gelatinous coating. The particles dry and can be administered in any of the methods described herein, e.g., by stirring into water and consumed as a drink, being placed into a capsule and swallowed, or through a delivery tube.

A beneficial substance according to the invention may also be directly delivered in any manner directly into the gastrointestinal tract, preferably downstream of the stomach directly into the intestines, most preferably into the jejunum. Some known techniques for placing a delivery tube into the intestine, and that may be used to practice the invention, include: (1) placement of a percutaneous endoscopic gastrostomy (PEG) tube and passing a weighted or non-weighted feeding tube into the duodenum or jejunum; (2) surgically placing a direct jejunostomy tube; or, (3) placing a tube directly into the jejunum with a known PEG-like procedure, whereby the jejunum is accessed by stab-piercing the jejunum from outside the abdominal wall. Other methods that may be used to practice the invention, and that are currently used for enteral delivery of fluids, are disclosed in U.S. Pat. Nos. 5,562,615; 4,487,604; 4,498,843; 4,518,327; 4,515,584; 4,636,144; 4,832,584; 4,884,013; 4,913,703 and 5,251,027, the respective disclosures of which are incorporated herein by reference. A beneficial substance may also be delivered by a surgically formed gastrostomy or by a percutaneous endoscopic technique requiring no laparotomy as disclosed in, for example, Gauderer & Ponsky, "A Simplified Technique For Constructing A Tube Feeding Gastrostomy," *Surgery, Gynecology & Obstetrics*, vol. 152, pp. 82–85 (June 1981), the disclosure of which is incorporated herein by reference.

One preferred method for delivering a beneficial substance directly into the intestinal tract is disclosed in U.S. Pat. No. 4,594,074, the disclosure of which is incorporated herein by reference. This patent discloses an enteral tube feeding device. Enteral feeding usually involves the use of a percutaneous access catheter, such as a gastrostomy feeding tube, for introducing food and/or medicine directly into the gastrointestinal tract. The administered substance is usually a liquid conveyed directly into the intestinal tract by a nasogastrointestinal tube, generally referred to as an enteral feeding tube. U.S. Pat. No. 4,594,074 basically discloses an enteral feeding tube utilizing a tube insert or bolus disposed on a distal end of the tube. The bolus contains at least one opening defining the tube outlet and has an internal design that substantially approximates the fluid flow characteristics of an open-ended tube yet does not easily become occluded with mucous and feeding material.

Referring now to FIG. 1, a preferred delivery tube 10 is a nasogastrointestinal feeding tube of the type described in U.S. Pat. No. 4,594,074. Tube 10 has a first end 10A positioned outside of the subject's nose and a second end 10B positioned downstream of the stomach, inside the jejunum. Alternatively, a preferred delivery tube according to the invention may have a first end at any position outside of the intestines, such as outside of the mouth, and a second end preferably positioned downstream of the stomach, so that a beneficial substance introduced into the first end exits the second end at a point downstream of the stomach.

Another preferred method for delivering a beneficial substance directly into the intestinal tract is disclosed in U.S. Pat. No. 4,795,430, the disclosure of which is incorporated herein by reference. This patent discloses a device for intubating an ostomy, as for example, a gastrostomy, formed by a percutaneous endoscopic technique. The device employs a multi-lumen enteral feeding tube, preferably having at least a fluid delivery lumen and an inflation lumen. The tube includes a port near one end to dispose the inflation lumen to ambient air and an outlet at the other end to convey fluid from within the fluid lumen into the patient. A retention member, preferably an inflatable cuff, is joined near the other end of the tube. The device is utilized to intubate a gastrostomy formed by a percutaneous endoscopic technique.

A beneficial substance according to the invention is introduced into a delivery tube, such as any of the described enteral feeding tubes, preferably by first wetting the particulate beneficial substance and then placing it in the tube's conduit, where it is conveyed directly to the gastrointestinal tract, preferably downstream of the stomach and most preferably to the jejunum. This may be done by placing the particulate beneficial substance into a syringe and adding water so that the beneficial substance is dispersed (preferably homogeneously) throughout the water. This dispersion can then be placed directly into the conduit, to a line going to the conduit or to a reservoir of fluid leading to the conduit, so it an be delivered directly into the gastrointestinal track.

Additionally, it is possible to include a beneficial substance according to the invention in the form of a tablet or capsule. Any capsule or tablet suitable for at least partially protecting the probiotic as it passes through the stomach, thus allowing a greater amount of probiotic to enter the large intestine than would enter without use of the capsule or tablet, may be used. Such a tablet may have a generally homogenous composition or include individual layers containing the various constituents of the tablet (such as the probiotic and prebiotic).

Tablets according to the invention can be produced in any suitable manner, and two particular methods are described herein. First, the powder mixtures of carriers and auxiliaries (e.g., release agents) and active ingredients (probiotics, vitamins, prebiotics, etc.) may be placed in a commercially available tabletting machine in one or more layers. The probiotic should not be exposed to any constituent that would destabilizing or destroy it. Each ingredient should be well dried and preferably have a water content of 0.1% or less. The powdered constituents are then tabletted to form a tablet. The press pressure is preferably between 50 and 120 Newtons.

Alternatively, individual layers of, for example, probiotic and prebiotic, can be formed separately, with press pressures preferably between 20 and 80 Newtons used for the individual layers. The layers preformed in this way are then pressed at press pressures of between 50 and 120 Newtons to create the finished multilayer tablet. This pressing method has the advantage that the layers which have a different compressibility on account of their different composition can be exposed to individual press pressures, which can be advantageous both with respect to the shelf life of the multilayer tablet as a whole and with respect to the stability of active ingredients in the individual layers. In addition, the boundary layer between two layers in juxtaposition has a smaller active surface due to the preforming, whereby the possibility of the reaction or destabilization of sensitive active ingredients, including the probiotic, is reduced.

Another method of encapsulating a beneficial substance according to the invention is disclosed in U.S. Pat. No. 6,309,666, the disclosure of which, except for the Abstract and Background sections, are incorporated herein by reference.

Having described preferred embodiments of the invention, alterations and modifications within its scope may occur to others. The scope of the invention is not limited to the particular examples, process steps, or materials disclosed as preferred embodiments but is instead set forth in the appended claims and legal equivalents thereof.

What is claimed is:

1. A composition comprising a probiotic and a prebiotic with the proviso that the prebiotic is not agar.
2. The composition of claim 1 wherein the probiotic comprises one or more bacteria from the group consisting of Bifidobacteria and *Lactobacillus*.
3. The composition of claim 1 wherein the prebiotic comprises a mucopolysaccharide.
4. The composition of claim 3 that further comprises pectin.
5. The composition of claim 3 wherein the prebiotic comprises one or more of the group consisting of chitin, and carraganan.
6. The composition of claim 3 wherein the prebiotic comprises chitin.
7. The composition of claim 3 wherein the probiotic comprises one or more of the bacteria of the group consisting of Bifidobacteria and Lactobacilli.
8. The composition of claim 3 wherein the probiotic comprises a Lactobacilli.
9. The composition of claim 8 wherein the probiotic comprises one or more of the group comprising *L. acidophilus, L. casei, L. fermentum, L. salivaroes, L. brevis, L. leichmannii, L. plantarum* and *L. cellobiosius*.
10. The composition of claim 3 wherein the probiotic comprises *B. adolescentis*.
11. The composition of claim 3 wherein the probiotic comprises *L. acidophilus*.
12. The composition of claim 3 that is formed as part of a tablet.
13. The composition of claim 3 that is contained within a capsule.
14. The composition of claim 3 that includes $10^6$ or more probiotic.
15. The composition of claim 3 that includes 0.1–10% probiotic and 90–99.9% prebiotic.
16. The composition of claim 3 that further comprises an oligosaccharide.
17. The composition of claim 15 that further comprises an oligosaccharide.
18. A method of directly introducing into the gastrointestinal tract of a human, downstream of the stomach, the composition of claim 1.
19. A method of directly introducing into the gastrointestinal tract of a human, downstream of the stomach, the composition of claim 3.
20. The method of claim 18 wherein the composition of claim 1 is introduced directly into the jejunum.
21. The method of claim 19 wherein the composition of claim 3 is introduced directly into the jejunum.
22. The composition of claim 3 wherein the composition is agglomerated into particles and then dried.
23. A method of introducing into the intestinal tract of a human, downstream of the stomach, a beneficial substance, by utilizing a delivery tube having a first end upstream of the stomach and a second end in the gastrointestinal tract downstream of the stomach, the method comprising:

(a) introducing the beneficial substance into the first end of the delivery tube; and
(b) allowing the beneficial substance to exit the second end of the delivery tube where it enters the intestinal tract downstream of the stomach.

24. The method of claim 23 wherein the beneficial substance is a prebiotic.
25. The method of claim 23 wherein the beneficial substance is a probiotic.
26. The method of claim 23 wherein the beneficial substance is a composition comprising a prebiotic and a probiotic.
27. The method of claim 23 wherein the second end of the delivery tube is in the jejunum.
28. The method of claim 23 wherein the first end of the delivery tube is outside of the nose.
29. The method of claim 24 wherein the prebiotic includes an AG.
30. The method of claim 26 wherein the prebiotic includes an AG.
31. The method of claim 24 wherein the prebiotic includes a non-starch polysaccharide.
32. The method of claim 26 wherein the prebiotic includes a non-starch polysaccharide.
33. The method of claim 24 wherein the prebiotic includes a mucopolysaccharide.
34. The method of claim 26 wherein the prebiotic includes a mucopolysaccharide.
35. The method of claim 24 wherein the prebiotic includes an oligosaccharide.
36. The method of claim 26 wherein the prebiotic includes an oligosaccharide.
37. The method of claim 36 wherein the prebiotic includes a FOS.
38. The method of claim 37 wherein the prebiotic includes a FOS.
39. The method of claim 25 wherein the probiotic includes a Bifidobacteria.
40. The method of claim 26 wherein the probiotic includes a Bifidobacteria.
41. The method of claim 40 wherein the probiotic includes *B. adolescentis*.
42. The method of claim 41 wherein the probiotic includes *B. adolescentis*.
43. The method of claim 25 wherein the probiotic includes *Bacteroides*.
44. The method of claim 26 wherein the probiotic includes *Bacteroides*.
45. The method of claim 25 wherein $10^6$ or greater probiotic are introduced into the first end of the delivery tube.
46. The method of claim 26 wherein $10^6$ or greater probiotic are introduced into the first end of the delivery tube.
47. The method of claim 24 wherein the prebiotic includes inulin.
48. The method of claim 26 wherein the prebiotic includes inulin.

49. The method of claim 23 wherein the delivery to be is an enteral tube feeding device.

50. The method of claim 26 wherein the composition comprises 0.1–10% probiotic and 90–99.9% prebiotic.

51. The method of claim 26 wherein the composition comprises 1–10% probiotic and 90–99% prebiotic.

52. The method of claim 26 wherein the composition comprises 0.1–99% probiotic and 1–99.9% prebiotic.

53. The method of claim 24 wherein the prebiotic comprises one or more of the group consisting of chitin, and carraganan.

54. The method of claim 26 that comprises a mucopolysaccharide and an oligopolysaccharide.

55. The method of claim 26 wherein the prebiotic comprises one or more of the group consisting of chitin, and carraganan.

56. The method of claim 24 wherein the prebiotic has a particle size of 25 microns or less.

57. The method of claim 26 wherein the prebiotic has a particle size of 25 microns or less.

58. The method of claim 26 wherein the probiotic has a particle size of 25 microns or less.

59. The method of claim 23 wherein an enteral food is also introduced into the first end of the delivery tube and allowed to exit the second end of the delivery tube.

* * * * *